United States Patent
Morini et al.

(10) Patent No.: US 6,841,632 B2
(45) Date of Patent: Jan. 11, 2005

(54) COMPONENTS AND CATALYSTS FOR THE (CO)POLYMERIZATION OF OLEFINS

(75) Inventors: Giampiero Morini, Padua (IT); Giulio Balbontin, Ferrara (IT); Ronald R. Andrea, IJsselstein (NL); Van Loon Jan Dirk, Almere (NL)

(73) Assignee: Basell Poliolefine Italis S.p.A., Milan (IT)

( * ) Notice: Subject to any disclaimer, the term of this patent is extended or adjusted under 35 U.S.C. 154(b) by 79 days.

(21) Appl. No.: 10/344,616
(22) PCT Filed: Jun. 10, 2002
(86) PCT No.: PCT/EP02/06805
§ 371 (c)(1),
(2), (4) Date: Feb. 12, 2003
(87) PCT Pub. No.: WO02/100904
PCT Pub. Date: Dec. 19, 2002

(65) Prior Publication Data
US 2004/0014597 A1 Jan. 22, 2004

(30) Foreign Application Priority Data
Jun. 13, 2001 (EP) ............................................. 01202290

(51) Int. Cl.$^7$ ................................................. C08F 4/42
(52) U.S. Cl. ................. 526/124.3; 526/348; 526/124.2; 526/123.1; 526/142; 502/127; 502/103; 502/115
(58) Field of Search ............................. 526/124.3, 348, 526/124.2, 123.1, 142; 502/127, 103, 115

(56) References Cited

U.S. PATENT DOCUMENTS

| | | | |
|---|---|---|---|
| 4,107,414 A | 8/1978 | Giannini et al. | ............ 526/114 |
| 4,220,554 A | 9/1980 | Scata et al. | ............ 252/429 B |
| 4,226,741 A | 10/1980 | Luciani et al. | .......... 252/429 B |
| 4,298,718 A | 11/1981 | Mayr et al. | ................. 526/125 |
| 4,399,054 A | 8/1983 | Ferraris et al. | ......... 252/429 B |
| 5,902,765 A * | 5/1999 | Takahashi et al. | .......... 502/127 |
| 2001/0025006 A1 | 9/2001 | Gao et al. | ................... 502/126 |

FOREIGN PATENT DOCUMENTS

| | | | |
|---|---|---|---|
| EP | 45977 | 1/1987 | ........... C08F/10/00 |
| EP | 344755 | 12/1989 | ............. C08F/4/02 |
| EP | 0 361 493 A1 * | 4/1990 | |
| EP | 361493 | 4/1990 | ........... C07C/43/10 |
| EP | 0 361 494 A2 * | 4/1990 | |
| EP | 361494 | 4/1990 | ........... C08F/4/654 |
| EP | 0 362 705 A2 * | 4/1990 | |
| EP | 362705 | 4/1990 | ........... C08F/10/00 |
| EP | 0 487 035 A2 * | 5/1992 | |
| EP | 0 487 035 * | 5/1992 | |
| EP | 487035 | 5/1992 | ........... C07C/43/10 |
| JP | 08165311 | 6/1996 | ........... C08F/4/654 |
| JP | 09095460 | 4/1997 | ........... C07C/43/04 |
| JP | 09309853 | 12/1997 | ........... C07C/43/15 |
| WO | 0142317 | 6/2001 | |

OTHER PUBLICATIONS

J. March, "Alkylation at a Carbon Bearing an Active Hydrogen;" *Advanced Organic Chemistry*; IV Edition (p. 464–468) 1992.

J. March, Sections 9–42 through 9–72; *Advanced Organic Chemistry*; IV Edition (p. 1214–1238) 1992.

* cited by examiner

Primary Examiner—Ling-Siu Choi

(57) ABSTRACT

Solid catalyst components comprising Ti,Mg, halogen and internal electron-donor compound selected from the 1,3-diethers of formula (I) in which R is a $C_1$–$C_{10}$ alkyl group, $R_1$ is a linear or branched primary alkyl radical having at least three carbon atoms, optionally containing a heteroatom, and $R_2$ is a secondary alkyl or cycloalkyl radicals different from i-propyl, optionally containing a heteroatom. The catalysts obtained by using as internal electron-donor compound the said 1,3-diethers display in the (co)polymerization of olefins an excellent balance of activity and stereospecificity that cannot be reached with the ethers known in the art.

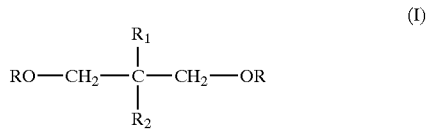

(I)

17 Claims, No Drawings

COMPONENTS AND CATALYSTS FOR THE (CO)POLYMERIZATION OF OLEFINS

This application is the U.S. national phase of International Application PCT/EP02/06805, filed Jun. 10, 2002.

The present invention relates to solid components of catalysts for the (co)polymerization of olefins and the catalysts obtained therefrom. In particular, the present invention relates to Ziegler-Natta catalyst component suitable for the (co)polymerization of propylene and comprising Ti, Mg, halogen and a specific electron-donor compound. The catalysts including titanium compounds supported on magnesium halides are well known in the art. Catalysts of this type are described in the U.S. Pat. No. 4,298,718. Said catalysts comprise titanium tetrahalides supported on halides of magnesium. Although the catalysts have high activity in the polymerization of alpha olefins like propylene, they are not very stereospecific. Improvements to stereospecificity have been made by adding electron-donor compounds to the solid catalyst component Substantial improvements were made using, in addition to the electron-donor present in the solid component, an electron-donor added to the aluminium alkyl co-catalyst component (U.S. Pat. No. 4,107,414). The catalysts modified in this manner although being highly stereospecific (Isotactic Index about 94–95%) still do not show sufficiently high levels of activity. Significant improvements in activity and stereospecificity were obtained by preparing the solid catalytic component according to the technique described in U.S. Pat. No. 4,226,741. High level performance in catalyst activity as well as stereospecificity have been obtained with the catalysts described in the European patent No. 045977. Said catalysts have as solid catalysts component, a magnesium halide on which is supported a titanium halide, preferably $TiCl_4$, and an electron-donor compound, selected from specific classes of carboxylic acid esters, and, as co-catalyst component, a system formed of an Al-trialkyl compound and a silicon compound containing at least one Si—OR bond (R hydrocarbyl radical). Nevertheless the results described above, research activities have been continued with the purpose of modifying and/or improving the performance of the mentioned catalysts. The European patent No. 0361494 describes solid catalyst components for the polymerization of olefins comprising, as an internal electron-donor compound, an ether containing two or more ether groups and having specific reaction characteristics toward the anhydrous magnesium chloride and $TiCl_4$. The catalysts obtained from the reaction of said catalyst components with an Al-alkyl compound exhibit a so high activity and stereospecificity in the polymerization of olefins, that the use of an external electron-donor can be avoided.

Due to the fact that the field of the polymerization of olefins is highly competitive it is clear that it is always felt the need of improving the performances with the respect to what is already known in the art. Now the applicant has surprisingly found new catalyst components having such improved characteristics. In fact, it has been found that the catalysts obtained by using as internal electron-donor compounds the 1,3-diethers of formula (I) in which R is a $C_1$–$C_{10}$ alkyl group, $R_1$ is a linear or branched primary alkyl group containing at least three carbon atoms, and optionally containing a heteroatom and $R_2$ is a secondary alkyl or cycloalkyl different from i-propyl and optionally containing a heteroatom, display, in the (co)polymerization of olefins, an excellent balance of activity and stereospecificity that cannot be reached with the ethers known in the art.

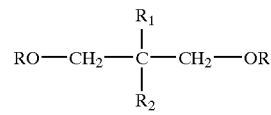

(I)

The present invention provides a solid catalyst component for the (co)polymerization of olefins $CH_2$=CHR, in which R is hydrogen or hydrocarbyl radical with 1–12 carbon atoms comprising Mg, Ti halogen and the 1,3-diethers of formula (1). Particularly preferred are the solid catalyst components comprising a titanium compound, containing at least one Ti-halogen bond, and an internal electron-donor compound chosen from the above mentioned 1,3-diethers, supported on magnesium halide. In another preferred embodiment of the said solid catalyst components Mg-halide is in active form. The active form of the magnesium halides present in the catalyst components of the invention is recognizable by the fact that in the X-ray spectrum of the catalyst component the major intensity reflection which appears in the spectrum of the nonactivated magnesium halides (having surface area smaller than 3 $m^2/g$) is no longer present, but in its place there is a halo with the position of the maximum intensity shifted with respect to the position of the major intensity reflection, or by the fact that the major intensity reflection presents a half-peak breadth at least 30% greater that the one of the corresponding reflection of the nonactivated Mg halide. The most active forms are those in which the halo appears in the X-ray spectrum of the solid catalyst component. Among the magnesium halides, the chloride is the preferred compound. In the case of the most active forms of the magnesium chloride, the halo appears in place of the reflection which in the spectrum of the nonactivated magnesium chloride is situated at the interplanar distance of 2.56 Å. In the 1,3-diethers of formula (I) R is preferably a methyl group, $R_1$ is preferably a $C_4$–$C_7$ linear or branched primary alkyl radical, optionally containing a heteroatom, and $R_2$ is preferably a cycloalkyl or a ($R_3$>CH— radical, where the $R_3$ groups, same or different, are $C_1$–$C_{10}$ linear alkyl radicals, provided that they are not contemporarily $CH_3$; said $R_3$ groups optionally containing a heteroatom selected from halogens, in particular F. Particularly preferred are the $R_2$ groups selected from $C_3$–$C_5$ secondary alkyl radicals or $C_5$–$C_7$ cycloalkyl. $R_1$ is preferably selected from the group consisting of n-butyl, n-pentyl n-hexyl, n-heptyl, i-butyl and i-pentyl, $R_2$ is preferably selected from the group consisting of sec-butyl, 3-pentyl, (1-trifluoromethyl)ethyl, cyclopentyl, cyclohexyl and cycloheptyl.

Examples of representative 1,3 diethers that are included in the above formula (I) are: 2-n-propyl-2-sec-butyl-1,3-dimethoxypropane, 2-n-butyl-2-sec-butyl-1,3-dimethoxypropane, 2-n-butyl-2-(3-pentyl)-1,3-dimethoxypropane, 2-n-pentyl-2-sec-butyl-1,3dimethoxypropane, 2-n-propyl-2-cyclopentyl-1,3dimethoxypropane, 2-n-propyl-2-cyclohexyl-1,3-dimethoxypropane, 2-n-butyl-2-cyclopentyl-1,3-dimethoxypropane, 2-n-butyl-2-cyclohexyl-1,3-dimethoxypropane, 2-n-butyl-2-cycloheptyl-1,3-dimethoxypropane, 2-n-pentyl-2-cyclopentyl-1,3-dimethoxypropane, 2-n-pentyl-2-cyclohexyl-1,3-dimethoxypropane, 2-n-hexyl-2-cyclopentyl-1,3-dimethoxypropane, 2-n-heptyl-2-cyclopentyl-1,3-dimethoxypropane, 2-i-butyl-2-(3-pentyl)-1,3-dimethoxypropane, 2-1-butyl-2-cycloheptyl-1,3-dimethoxypropane, 2-1-pentyl-2-cyclopentyl 1,3- dimethoxypropane, 2-i-butyl-2-(1-trifluoromethyl)ethyl-1, 3-dimethoxypropane. 1,3-diethers particularly preferred are: 2-n-butyl-23-pentyl)1,3-dimethoxypropane, 2-n-pentyl-2-sec-butyl-1,3-dimethoxypropane, 2-n-propyl-2-cyclohexyl-1,3-dimethoxypropane, 2-n-butyl-2-cyclohexyl-1,3 dimethoxypropane, 2-n-pentyl-2-cyclohexyl-1,3-dimethoxypropane, 2-n-hexyl-2-cyclopentyl-1,3-dimethoxypropane, 2-1-butyl-2-cycloheptyl-1,3-dimethoxypropane, 2-1-pentyl-2-cyclopentyl-1,3-dimethoxypropane, 2-i-butyl-2-(1-trifluoromethyl)ethyl-1, 3-dimethoxypropane.

The 1,3-diethers of the present invention can be prepared according to the methods disclosed in the European patent application No. 0361493. Said diethers, used in the preparation of Ziegler-Natta catalysts, are generally synthesized by the reaction of alkylating agents with the diols corresponding to the above diethers. A way of synthesis of said diols consists in the reduction of the corresponding malonates.

The preparation of the solid catalyst components can be carried out using various methods. For example, the magnesium halide (preferably used in a form containing less than 1% of water), the titanium compound and the electron-donor compound are milled together under conditions that cause the activation of the magnesium halide; the milled product is then caused to react one or more times with $TiCl_4$ in excess, optionally in the presence of an electron-donor, at a temperature ranging from 80 to 135° C., and then repeatedly washed with a hydrocarbon (such as hexane) until no chlorine ions can be detected in the wash liquid. According to another method, the anhydrous magnesium halide is preactivated according to known methods and then reacted with an excess of $TiCl_4$ containing the electron-donor compound and optionally an aliphatic, cycloaliphatic, aromatic or chlorinated hydrocarbon solvent (for example hexane, heptane, cyclohexane, toluene, ethylbenzene, chlorobenzene, dichloroethane). In this case also the operation takes place at a temperature between 800 and 135° C. The reaction with $TiCl_4$, in the presence or absence of an electron-donor, is optionally repeated and the solid is then washed with hexane to eliminate the nonreacted $TiCl_4$. According to a preferred method, a $MgCl_2 \cdot nROH$ adduct (particularly in the form of spheroidal particles) where n is generally from 1 to 6, and ROH is an alcohol, preferably ethanol, is caused to react with an excess of $TiCl_4$ containing the electron-donor compound and optionally one of the above mentioned hydrocarbon solvents. The reaction temperature initially is from 0° to 25° C., and is then increased to 80–135° C. Then, the solid is reacted once more with $TiCl_4$, in the presence or absence of the electron-donor, separated and washed with a hydrocarbon until no chlorine ions can be detected in the wash liquid. According to yet another method, magnesium alcoholates and chloroalcoholates (the chloroalcoholates can be prepared particularly as described in U.S. Pat. No. 4,220,554) are caused to react with $TiCl_4$ in excess containing the electron-donor compound, operating under the reaction conditions already described. According to a further method, complexes of magnesium halides with titanium alcoholates (the $MgCl_2 \cdot 2Ti(OC_4H_9)_4$ complex is a typical example) are caused to react, in a hydrocarbon solution, with $TiCl_4$ in excess containing the electron-donor compound; the separated solid product is reacted again with an excess of $TiCl_4$, in the presence or absence of electron-donor, and then separated and washed with hexane. The reaction with $TiCl_4$ is carried out at a temperature ranging from 80° to 130° C. According to a variance of the latter method, the $MgCl_2$ and titanium alcoholate complex is caused to react in a hydrocarbon solution with polyhydrosiloxane; the separated solid product is reacted at 50° C. with silicon tetrachloride containing the electron-donor compound; the solid is then reacted with $TiCl_4$ in excess, in the presence or absence of electron-donor, operating at 80°–130° C.

Independently from the specific preparation method, after the last reaction with $TiCl_4$ in the presence of the electron-donor, it is preferable to separate the solid obtained (by way of filtration, for example), and cause it to react with an excess of $TiCl_4$ at temperatures ranging from 80° to 135° C., before washing it with the hydrocarbon solvent.

Finally, it is possible to cause to react $TiCl_4$ in excess and containing the electro-donor with porous resins such as partially cross-linked styrene-divinylbenzene in spherical particle form, or porous inorganic oxides such as silica and alumina, impregnated with solutions of magnesium compounds or complexes soluble in organic solvents. The porous resins which can be used are described in the European patent application No. 0344755. The reaction with $TiCl_4$ is carried out at 80–100° C. After separating the excess of $TiCl_4$, the reaction is repeated and the solid is then washed with a hydrocarbon. The $MgCl_2$/electron-donor molar ratio used in the reactions indicated above generally ranges from 2:1 to 30:1, preferably from 4:1 to 12:1. The electron-donor compound is fixed on the magnesium halide in a quantity generally ranging from 1 to 25% molar with respect to $MgCl_2$. In particular, the 1,3-diethers of formula (1) are present on the catalyst component in a quantity generally ranging from 5 to 30% weight, preferably from 8 to 25% weight. In the solid catalyst components the Mg/Ti molar ratio is generally from 30:1 to 3:1; in the components supported on resins or on inorganic oxides the ratio can be different and usually ranges from 20:1 to 2:1. The titanium compounds that can be used for the preparation of the catalyst components are the halides or the compounds of formula $TiX_n(OR^4)_{4-n}$, where $0<n\leq 3$, X is halogen, preferably chlorine, and R is $C_1$–$C_{10}$ hydrocarbon group. The titanium tetrachloride is the preferred compound. Satisfactory results can also be obtained with the trihalides, particularly $TiCl_3$ HR, $TiCl_3$ ARA and with the halogen alcoholates such as $TiCl_3$ OR, where R is a $C_1$–$C_{10}$ hydrocarbon radical. The solid catalyst components of the invention form, by reaction with the Al-alkyl compounds, catalysts which can be used in the (co)polymerization of $CH_2=CHR$ olefins, where R has the meaning given above. Therefore, the present invention provides a catalyst for the (co) polymerization of olefins comprising the reaction product of:

a) a catalyst component as defined above;
b) an Al-alkyl compound and optionally
c) an electron-donor compound.

The Al-alkyl compounds comprise Al-trialkyls such as Al-triethyl, Al-triisobutyl, Al-tri-n-butyl, Al-trioctyl and alkyl aluminium halides, such as $AlEt_2Cl$ and $Al_2Et_3Cl_3$. Also linear or cyclic Al-alkyl compounds containing one or more Al atoms bonded to one another with O, N, or S atoms can be used.

The Al-Alkyl compound is used in Al/Ti ratios generally ranging from 1 to 1000.

The trialkyl compounds can also be used in blends with Al-alkyl halides such as $AlEt_2Cl$ and $AlEt_{3/2}Cl_{3/2}$. The polymerization of the olefins is carried out according to known methods operating in liquid phase constituted by one or more monomers, or by a solution of one or more monomers in an aliphatic or aromatic hydrocarbon solvent, or in gas phase, or also by combining polymerization stages in liquid phase and in gas phase. The (co)polymerization temperature is usually from 0 to 150° C.; particularly from 60° to 100° C. The operation occurs at atmospheric pressure or higher. The catalysts can be precontacted with small quantities of olefins (prepolymerization). The prepolymerization improves the performance of the catalysts as well as the morphology of the polymers. The prepolymerization is carried out maintaining the catalysts in suspension in a hydrocarbon solvent (hexane or heptane, for example), adding an olefin, and operating at temperatures ranging from room temperature to 60° C. producing a quantity of polymer generally from 0.5 to 50 times the weight of the catalyst. It can also be carried out in liquid monomer, under the temperature conditions indicated above, and producing quantities of polymer which can reach 1000 g per g of catalytic component. As explained above the said catalysts show an excellent balance of activity and stereospecificity in the stereoregular polymerization of olefins even without the use of an external donor. If desired however, this latter can be added to the Al-alkyl compound and, in this case, the said external electron-donor can preferably be selected from the group consisting of silicon compounds containing at least one Si—OR bond (R is a hydrocarbon radical); 2,2,6,6-tetramethylpiperidine; 2,6-diisopropylpiperidine; carboxylic acid esters, such as ethylparatoluate and ethylbenzoate, and di- and polyethers. Preferably, the silicon compounds have the formula $R^5_q Si(OR^6)_{4-q}$ where q is from 1 to 3, the $R^5$ radical or radicals, same or different, are $C_1$–$C_{12}$ alkyl, $C_3$–$C_{12}$ cycloalkyl, $C_6$–$C_{12}$ aryl, $C_1$–$C_{12}$ alkaryl or aralkyl radicals, $R^7$-N—$R^8$ radicals, where $R^7$ and $R^8$ are the same or different and have the same meaning defined above for $R^5$, or are bonded to each other to form a cyclic structure; the $R^6$ radicals are the same or different and are $C_1$–$C_6$ alkyl radicals. Optionally the $R^5$ to $R^8$ radicals can contain one or more halogens, in particular Cl and F, as substitutes for hydrogen atoms.

Examples of said compounds are: (tert-butyl)$_2$Si(OCH$_3$)$_2$; (cyclohexyl)$_2$Si(OCH$_3$)$_2$; (isopropyl)$_2$Si(OCH$_3$)$_2$; (sec-butyl)$_2$Si(OCH$_3$)$_2$; (cyclohexyl)(methyl)Si(OCH$_3$)$_2$; (cyclopentyl)$_2$Si(OCH$_3$)$_2$; (isopropyl)(methyl)Si(OCH$_3$)$_2$; (n-butyl)$_2$Si(OCH$_3$)$_2$; (isobutyl)$_2$Si(OCH$_3$)$_2$; (sec-butyl)$_2$Si(OCH$_3$)$_2$; (tert-butyl)(methyl)Si(OCH$_3$)$_2$; (tert-amyl)(methyl)Si(OCH$_3$)$_2$; (tert-hexyl)(methyl)Si(OCH$_3$)$_2$; (2-norbornyl)(methyl)Si(OCH$_3$)$_2$; (tert-butyl)(cyclopentyl)Si(OCH$_3$); (2-norbornyl)(cyclopentyl)Si(OCH$_3$)$_2$; (tert-butyl)Si(OCH$_3$)$_3$; (tert-butyl)Si(OCH$_3$)$_3$; (2-norbornyl)Si(OCH$_3$)$_3$; (2-norbornyl)Si(OCH$_3$)$_3$; (tert-hexyl)Si(OCH$_3$)$_3$; (tert-hexyl)Si(OC$_2$H$_5$)$_3$; (tert-butyl)(2-methylpiperidyl)Si(OCH$_3$)$_2$; (tert-butyl)(3-methylpiperidyl)Si(OCH$_3$)$_2$; (tert-butyl)(4methylpiperidyl)Si(OCH$_3$)$_2$; (tert-hexyl)(piperidyl)Si(OCH$_3$)$_2$; (tert-hexyl)(pyrrolidinyl)Si(OCH$_3$)$_2$; (methyl)(3,3,3-trifluoropropyl)Si(OCH$_3$)$_2$; (isopropyl)(3,3,3-trifluoropropyl)Si(OCH$_3$)$_2$; (n-butyl)(3,3,3-trifluoropropyl)Si(OCH$_3$)$_2$; (isobutyl)(3,3,3-trifluoropropyl)Si(OCH$_3$)$_2$; (sec-butyl)(3,3,3-trifluoropropyl)Si(OCH$_3$)$_2$; (tert-butyl)(3,3,3-trifluoropropyl)Si(OCH$_3$)$_2$; (3,3,3-trifluoropropyl)(piperidyl)Si(OCH$_3$)$_2$; (3,3,3-trifluoropropyl)(2-methylpiperidyl)Si(OCH$_3$)$_2$; (3,3,3-trifluoropropyl)(2-ethylpiperidyl)Si(OCH$_3$)$_2$; (3,3,3-trifluoropropyl)(3-methylpiperidyl)Si(OCH$_3$)$_2$; (3,3,3-trifluoropropyl)(4methylpiperidyl)Si(OCH$_3$)$_2$; (3,3,3-trifluoropropyl)$_2$Si(OCH$_3$)$_2$.

The molar ratio of the Al-alkyl compound to the external electron-donor generally is from 2:1 to 100:1 and preferably from 10:1 to 30:1; said ratio can be broader, for example from 0.5:1 to 100:1, during the prepolymerization phase. The catalysts find particular application in the (co)polymerization of CH$_2$=CHR olefins where R is hydrogen or a 1–6 carbon alkyl or aryl radical. In particular, said catalysts are suitable used for the stereospecific polymerization of propylene or its copolymerization with ethylene or other α-olefins such as 1-butene, 1-hexene and 1-octene. The following examples are given in order to illustrate and not limit the invention Unless otherwise indicated, the percentages in the examples are expressed by weight. The melt flow rate (MFR) for polypropylene is determined according to ASTM D1238, condition L. The intrinsic viscosity [η] is determined in tetrahydronaphthalene at 135° C. (ASTM 2857-70). In order to determine the fraction insoluble in xylene at 25° C. (X.I.%), 2.5 g of polymer are dissolved under agitation in 250 ml of xylene at 135° C., and after 20 minutes it is allowed to cool to 25C. After 30 minutes the precipitated polymer is filtered and dried at reduced pressure at 80° C. until constant weight is reached.
Synthesis of 13-diethers (I)

The 1,3-diethers of formula (I) used in the present invention have been prepared by alkylation of diethyl malonates (see J. March in "Advanced Organic Chemistry" IV Ed.; 1992; pp.464–468) followed by reduction to the corresponding diols (see "ibid" pp 1214) and methylation (see R. C. Larock in "Comprehensive organic transformations" Ed VCH 1989 pp.445–472).

EXAMPLE 1

Into a 500 ml four-necked round flask, purged with nitrogen, 250 ml of TiCl$_4$ were introduced at 0° C. While stirring, 10.0 g of microspheroidal MgCl$_2$·2.8 C$_2$H$_5$OH (prepared according to the method described in ex. 2 of U.S. Pat. No. 4,399,054 but operating at 3,000 rpm instead of 10,000) and 7.5 mmoles of 2-n-butyl-2-sec-butyl-1,3-dimethoxypropane were added. The temperature was raised to 100° C. and maintained for 120 min. Then, the stirring was discontinued, the solid product was allowed to settle and the supernatant liquid was siphoned off. 250 ml of fresh TiCl$_4$ were added. The mixture was reacted at 120° C. for 60 min and, then, the supernatant liquid was siphoned off. The solid was washed six times with anhydrous hexane (6×100 ml) at 60° C. Finally, the solid was dried under vacuum and analyzed.

The catalyst component obtained in this manner contains: Ti=4.6%; Mg=15.9%; 2-n-butyl-2-sec-butyl-1,3-dimethoxypropane=22.1%. In a 4 liter autoclave, previously purged with gaseous propylene at 70° C. for 1 hour, are introduced at room temperature and in propylene flow 70 ml of anhydrous n-hexane containing 7 mmoles of aluminum triethyl and 4 mg of the solid catalyst component prepared as described above. The autoclave is closed, 1.7 M of hydrogen and 1.2 kg of liquid propylene are introduced; the agitator is put in motion and the temperature is increased to 70° C. in a period of 5 minutes. After 2 hours at 70° C., the agitation is interrupted, the nonpolymerized monomer is removed, and the content is cooled to room temperature. The polymer yield is 103 Kg of polypropylene/g of solid catalyst component. Said polypropylene has a fraction insoluble in xylene at 25° C. (X.I.)=96.9%, a melt index MRL 5.2 g/10 min and an intrinsic viscosity [η]=1.7 dL/g.

EXAMPLES 2–10 AND COMPARATIVE EXAMPLES 11–13

The procedure of Example 1 is used, except that the 1,3-diethers of formula (I) reported in table 1 are used as internal electron-donor compounds. Also, in said table, are shown the composition of the catalyst components and the polymerization results.

TABLE 1

| example | 1,3-diether | Mg wt % | TI wt % | Ether wt % | Activity Kg/gcat | XI wt % |
|---|---|---|---|---|---|---|
| 2 | 2-n-butyl-2-(3-pentyl)-1,3-dimethoxypropane | 15.2 | 4.8 | 22 | 108 | 96.9 |
| 3 | 2-n-pentyl-2-sec-butyl-1,3-dimethoxypropane | 14.9 | 4.8 | 16.5 | 103 | 96.9 |
| 4 | 2-n-propyl-2-cyclohexyl-1,3-dimethoxypropane | 17.6 | 4.6 | 17.8 | 120 | 97.1 |
| 5 | 2-n-butyl-2-cyclohexyl-1,3-dimethoxypropane | 16.7 | 6.6 | 19.9 | 108 | 96.3 |
| 6 | 2-n-pentyl-2-cyclohexyl-1,3-dimethoxypropane | 14.7 | 4.8 | 19.2 | 95 | 96.8 |
| 7 | 2-n-hexyl-2-cyclopentyl-1,3-dimethoxypropane | 18.1 | 3.9 | 18.5 | 104 | 97.6 |
| 8 | 2-1-butyl-2-cycloheptyl-1,3-dimethoxypropane | 15.1 | 4.8 | 19.6 | 95 | 96.3 |
| 9 | 2-1-pentyl-2-cyclopentyl-1,3-dimethoxypropane | 16.7 | 4.7 | 17.9 | 101 | 97.2 |
| 10 | 2-1-butyl-2-(1-trifluoromethyl)ethyl-1,3-dimethoxypropane | 16.3 | 4.2 | 15.2 | 105 | 96.7 |
| Comp. 11 | 2-1-pentyl-2-1-propyl-1,3-dimethoxypropane | 19.4 | 3.6 | 16.8 | 80 | 97.7 |
| Comp. 12 | 2-1-butyl-2-1-propyl-1,3-dimethoxypropane | 18.0 | 4.2 | 17.3 | 70 | 96.0 |
| Comp. 13 | 2-i-propyl-2-cyclopentyl-1,3-dimethoxypropane | 19.6 | 4.5 | 16.5 | 81 | 96.4 |

What is claimed is:

1. A solid catalyst component for the (co)polymerization of olefins, comprising magnesium, titanium, halogen and a 1,3-diether of formula (I)

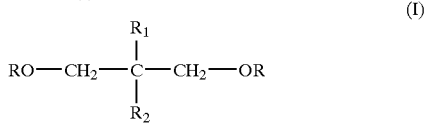

(I)

in which R is a $C_1$–$C_{10}$ alkyl group, $R_1$ is a linear or branched primary alkyl radical having at least three carbon atoms optionally containing a heteroatom, and $R_2$ is a secondary alkyl or cycloalkyl radical different from i-propyl, optionally containing a heteroatom.

2. The solid catalyst component according to claim 1 where $R_1$ is a $C_4$–$C_7$ linear or branched primary alkyl radical.

3. The solid catalyst component according to claim 1 in which $R_2$ is a cycloalkyl or $(R_3)_2$—CH— group, where the $R_3$ groups, same or different from each other, are $C_1$–$C_{10}$ linear alkyl radicals optionally containing a heteroatom, provided that said $R_3$ groups are not contemporarily $CH_3$.

4. The solid catalyst component according to claim 3 wherein $R_2$ groups are selected from the group consisting of $C_3$–$C_5$ secondary alkyl radicals and $C_5$–$C_7$ cycloalkyl radicals.

5. The solid catalyst component according to claim 1 in which the heteroatom is a halogen atom.

6. The solid catalyst component according to claim 5 in which the halogen atom is F.

7. The solid catalyst component according to claim 1 in which R is a methyl group.

8. The solid catalyst component of claim 2 wherein $R_1$ is n-butyl, n-pentyl, n-hexyl, n-heptyl, i-butyl or i-pentyl.

9. The solid catalyst component according to claim 3 in which $R_2$ is (1-trifluoromethyl)ethyl, sec-butyl, 3-pentyl, cyclopentyl, cyclohexyl or cycloheptyl.

10. The solid catalyst component according to claim 1, wherein the 1,3-diether (I) is 2-n-butyl-2-sec-butyl-1,3-dimethoxypropane, 2-n-butyl-2-(3-pentyl)-1,3-dimethoxypropane, 2-n-pentyl-2-sec-butyl-1,3-dimethoxypropane, 2-n-propyl-2-cyclohexyl-1,3-dimethoxypropane, 2-n-butyl-2-cyclohexyl-1,3-dimethoxypropane, 2-n-pentyl-2-cyclohexyl-1,3-dimethoxypropane, 2-n-hexyl-2-cyclopentyl-1,3-dimethoxypropane, 2-1-butyl-2-cycloheptyl-1,3-dimethoxypropane, 2-1-pentyl-2-cyclopentyl-1,3-dimethoxypropane or 2-1-butyl-2-(1-trifluoromethyl)ethyl-1,3-dimethoxypropane.

11. The solid catalyst component according to claim 1, where the titanium is a titanium compound containing at least a Ti-halogen bond supported on Mg dihalide.

12. The solid catalyst component according to claim 11 in which the titanium compound is a titanium halide or haloalcoholate.

13. The solid catalyst component according to claim 12, in which the titanium compound is titanium tetrachloride.

14. A catalyst for the (co)polymerization of olefins comprising the product of the reaction of:
a) a solid catalyst component for the (co)polymerization of olefins, comprising magnesium, titanium, halogen and a 1,3-diether of formula (I) in which R is a $C_1$–$C_{10}$ alkyl group, $R_1$ is a linear or branched primary alkyl radical having at least three carbon atoms optionally containing a heteroatom, and $R_2$ is a secondary alkyl or cycloalkyl radical different from i-propyl, optionally containing a heteroatom; with
b) an Al-alkyl compound and optionally
c) an electron-donor compound

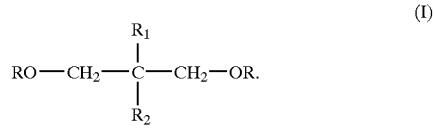

(I)

15. The catalyst according to claim 14 in which the Al-alkyl compound is an Al-trialkyl.

16. The catalyst according to claim 14 wherein the electron donor compound is selected from the group consisting of silicon compounds containing at least one Si—OR bond, where R is a hydrocarbon radical, 2,2,6,6-tetramethylpiperidine, 2,6-diisopropylpiperidine and carboxylic acid esters.

17. A process for the (co)polymerization of $CH_2$=CHR olefins, where R is hydrogen or $C_1$–$C_{10}$ hydrocarbyl radicals, said process being carried out in the presence of a catalyst for the (co)polymerization of olefins comprising the product of the reaction of:
a) a solid catalyst component for the (co)polymerization of olefins, comprising magnesium, titanium, halogen and a 1,3-diether of formula (I) in which R is a $C_1$–$C_{10}$ alkyl group, $R_1$ is a linear or branched primary alkyl radical having at least three carbon atoms optionally containing a heteroatom, and $R_2$ is a secondary alkyl or cycloalkyl radical different from i-propyl, optionally containing a heteroatom; with
b) an Al-alkyl compound and optionally
c) an electron-donor compound

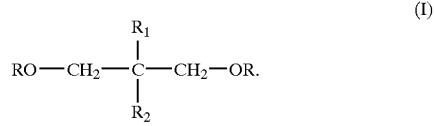

(I)

* * * * *